(12) United States Patent
Hayman et al.

(10) Patent No.: US 7,524,861 B2
(45) Date of Patent: Apr. 28, 2009

(54) PROCESS FOR THE PREPARATION OF A HYDRATE OF AN ANTHRANILIC ACID DERIVATIVE

(76) Inventors: David Frank Hayman, 957 Buckingham Avenue, Slough, Berkshire (GB) SL1 4NL; Michael Wright, 957 Buckingham Avenue, Slough, Berkshire (GB) SL1 4NL ( * ) Notice: Subject to any disclaimer, the term of this patent is extended or adjusted under 35 U.S.C. 154(b) by 458 days.

(21) Appl. No.: 10/513,986

(22) PCT Filed: May 13, 2003

(86) PCT No.: PCT/GB03/02060

§ 371 (c)(1),
(2), (4) Date: Apr. 8, 2005

(87) PCT Pub. No.: WO03/095447

PCT Pub. Date: Nov. 20, 2003

(65) Prior Publication Data

US 2005/0222199 A1    Oct. 6, 2005

Related U.S. Application Data

(60) Provisional application No. 60/379,759, filed on May 14, 2002.

(51) Int. Cl.
*C07D 401/12* (2006.01)
*A61K 31/47* (2006.01)
(52) U.S. Cl. .................. 514/307; 514/310; 546/140; 546/148

(58) Field of Classification Search .................. 546/140, 546/148
See application file for complete search history.

(56) References Cited

FOREIGN PATENT DOCUMENTS

EP            494623      *   7/1992
WO     WO 98/17648         4/1998

OTHER PUBLICATIONS

XENOVA Poster presented May 15, 2001 conference in USA entitled "A Phase IIA pharmacokinetic and pharmacodynamic study of the P-glycoprotein inhibitor, XR9576 in patients treated with doxorubicin chemitherapy".

* cited by examiner

*Primary Examiner*—Zinna N Davis
(74) *Attorney, Agent, or Firm*—Nixon & Vanderhye P.C.

(57) ABSTRACT

A hydrate of an acid addition bis-salt of an anthranilic acid derivative is produced by a process which comprises:
  (a) combining, in any order, the anthranalic acid derivative, a pharmaceutically acceptable organic solvent, an excess of water and a pharmaceutically acceptable strong acid to form a mixture;
  (b) warming the mixture until a clear solution forms;
  (c) filtering the solution while it is warm, to yield a filtrate; and
  (d) recovering the hydrate as defined above from the filtrate.

The hydrate has a defined number of moles of water of crystallization and possesses better storage stability and dissolution characteristics than conventionally produced hydrates of such acid addition bis-salts.

13 Claims, No Drawings

PROCESS FOR THE PREPARATION OF A HYDRATE OF AN ANTHRANILIC ACID DERIVATIVE

This application is the U.S. national phase of international application PCT/GB03/02060 filed 13 May 2003 which designated the U.S. and claims benefit of U.S. 60/379,759, dated 14 May 2002, the entire content of which is hereby incorporated by reference.

The present invention relates to hydrated forms of acid addition salts of anthranilic acid derivatives having activity as inhibitors of P-glycoprotein (P-gp), to their preparation and to pharmaceutical and veterinary compositions containing them.

WO-A-98/07648 describes a series of basic compounds having structures based on anthranilic acid, and acid addition salts thereof. These compounds have activity as inhibitors of P-glycoprotein (P-gp) and may be used as modulators of multidrug resistance, for instance in overcoming the multidrug resistance of tumours and pathogens. The compounds also have potential utility in improving the absorption, distribution, metabolism and elimination characteristics of certain drugs.

Many of the compounds of WO-A-98/07648 have two basic centres and consequently form acid addition bis-salts with salt-forming acids. The bis-salts are hydrated but do not exist as specific hydrates. Rather, they are obtained as indeterminate hydrates with a variable water content which have the disadvantage of being hygroscopic.

It has now surprisingly been found that the addition of excess water to the system comprising the dibasic starting compound and salt-forming acid promotes the dissolution of the dibasic compound and leads to the formation of the desired acid addition bis-salt as a defined hydrate. This hydrate is stable under controlled drying conditions.

Accordingly, the present invention provides a process for producing a hydrate of an acid addition bis-salt of a compound of formula (I):

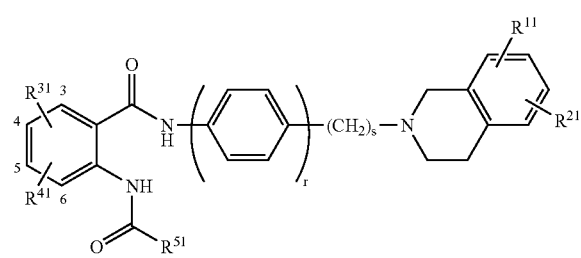

(I)

wherein $R^{11}$ and $R^{21}$, which may be the same or different, are each hydrogen or $C_1$-$C_6$ alkoxy;

$R^{31}$ and $R^{41}$, which may be the same or different, are each independently selected from H, $C_1$-$C_6$ alkyl, $CF_3$, a halogen, $NH_2$, $NO_2$, NHOH, $C_1$-$C_6$ alkoxy, hydroxy and phenyl; or $R^{31}$ and $R^{41}$, when situated on adjacent carbon atoms, form together with the carbon atoms to which they are attached a benzene ring or a methylenedioxy substituent, $R^{51}$ is a group selected from pyridine, quinoline, isoquinoline, 5,6,7,8-tetrahydroquinoline and 5,6,7,8-tetrahydroisoquinoline, the group being unsubstituted or substituted by $C_1$-$C_6$ alkyl or $C_1$-$C_6$ alkoxy;

r is 0 or 1, and s is 1, 2 or 3;

which process comprises:

(a) combining, in any order, a compound of formula (I) as defined above, a pharmaceutically acceptable organic solvent, an excess of water and a pharmaceutically acceptable strong acid, to form a mixture;

(b) warming the mixture until a clear solution forms;

(c) filtering the solution while it is warm, to yield a filtrate; and (d) recovering the hydrate as defined above from the filtrate.

The hydrate produced by the process of the present invention thus defined is also novel. Accordingly, the present invention further provides a hydrate of an acid addition salt of a compound of formula (I) as defined above, with a pharmaceutically acceptable strong acid, wherein the hydrate incorporates x moles of water of crystallisation per mole of the compound in which x is an integer of 1 to 6.

The integer x may be 1, 2, 3, 4, 5 or 6.

A $C_1$-$C_6$ alkyl group may be linear or branched. A $C_1$-$C_6$ alkyl group is typically a $C_1$-$C_4$ alkyl group, for example a methyl, ethyl, propyl, i-propyl, -butyl, sec-butyl or tert-butyl group. A halogen is F, Cl, Br or I. Preferably it is F, Cl or Br.

A $C_1$-$C_6$ alkoxy group may be linear or branched. It is typically a $C_1$-$C_4$ alkoxy group, for example a methoxy, ethoxy, propoxy, i-propoxy, n-propoxy, n-butoxy, sec-butoxy or tert-butoxy group.

The integer s is from 1 to 3, and is preferably 1 or 2. In a preferred series of compounds of formula (I) r is 1, s is 2, $R^{11}$ and $R^{21}$ are both methoxy and $R^{51}$ is a quinoline or tetrahydroquinoline ring system. $R^{51}$ is linked via any of its available ring positions, for instance the 1-, 2-, 3- or 4-position. Typically it is linked via the 2- or 3-position. Preferably $R^{51}$ is a 2-quinoline or 3-quinoline group. Groups $R^{11}$ and $R^{21}$ are preferably at positions 6 and 7 of the tetrahydroisoquinoline ring system.

Examples of compounds of formula (I) are as follows:

| Chemical Name | Compound No. |
| --- | --- |
| 2-Chloro-quinoline-3-carboxylic acid (2-{4-[2-(6,7-dimethoxy-3,4-dihydro-1H-isoquinolin-2-yl)-ethyl]-phenylcarbamoyl}-phenyl)-amide | 1 |
| 4-Hydroxy-7-trifluoromethyl-quinoline-3-carboxylic acid (2-{4-[2-(6,7-dimethoxy-3,4-dihydro-1H-isoquinolin-2-yl)-ethyl]-phenylcarbamoyl}-phenyl)-amide | 2 |
| Quinoline-3-carboxylic acid (2-{4-[2-(6,7-dimethoxy-3,4-dihydro-1H-isoquinolin-2-yl)-ethyl]-phenylcarbamoyl}-thiophen-3-yl)-amide | 3 |
| Quinoline-3-carboxylic acid (2-{4-[2-(6,7-dimethoxy-3,4-dihydro-1H-isoquinolin-2-yl)-ethyl]-phenylcarbamoyl}-4-dimethylamino- | 4 |

-continued

| Chemical Name | Compound No. |
|---|---|
| phenyl)-amide | |
| 4-Hydroxy-quinoline-3-carboxylic acid (2-{4-[2-(6,7-dimethoxy-3,4-dihydro-1H-isoquinolin-2-yl)-ethyl]-phenylcarbamoyl}-phenyl)-amide | 5 |
| Quinoline-3-carboxylic acid (3-{4-[2-(6,7-dimethoxy-3,4-dihydro-1H-isoquinolin-2-yl)-ethyl]-phenylcarbamoyl}-4-methyl-thiophen-2-yl)-amide | 6 |
| Quinoline-3-carboxylic acid [2-(4-{2-[(3,4-dimethoxy-benzyl)-methyl-amino]-ethyl}-phenylcarbamoyl)-phenyl]-amide | 7 |
| Quinoline-3-carboxylic acid (2-{4-[2-(6,7-dimethoxy-3,4-dihydro-1H-isoquinolin-2-yl)-ethyl]-phenylcarbamoyl}-4-methylsulfanyl-phenyl)-amide | 8 |
| Quinoline-3-carboxylic acid (4-{4-[2-(6,7-dimethoxy-3,4-dihydro-1H-isoquinolin-2-yl)-ethyl]-phenylcarbamoyl}-thiophen-3-yl)-amide | 9 |
| N-(4-{4-[2-(6,7-Dimethoxy-3,4-dihydro-1H-isoquinolin-2-yl)-ethyl]-phenylcarbamoyl}-thiophen-3-yl)-6-methyl-nicotinamide | 10 |
| Quinoline-3-carboxylic acid (2-{4-[2-(6,7-dimethoxy-3,4-dihydro-1H-isoquinolin-2-yl)-ethylsulfanyl]-phenylcarbamoyl}-phenyl)-amide | 11 |
| Quinoline-3-carboxylic acid (3-{4-[2-(6,7-dimethoxy-3,4-dihydro-1H-isoquinolin-2-yl)-ethyl]-phenylcarbamoyl}-pyrazin-2-yl)-amide | 12 |
| Quinoline-3-carboxylic acid (2-{4-[2-(6,7-dimethoxy-3,4-dihydro-1H-isoquinolin-2-yl)-ethoxy]-phenylcarbamoyl}-phenyl)-amide | 13 |
| Quinoline-3-carboxylic acid (2-{4-[2-(6,7-dimethoxy-1-methyl-3,4-dihydro-1H-isoquinolin-2-yl)-ethyl]-phenylcarbamoyl}-phenyl)-amide | 14 |
| Quinoline-3-carboxylic acid (2-{4-[2-(6,7-dichloro-3,4-dihydro-1H-isoquinolin-2-yl)-ethyl]-phenylcarbamoyl}-phenyl)-amide | 15 |
| Quinoline-3-carboxylic acid (2-{4-[2-(7,8-dichloro-3,4-dihydro-1H-isoquinolin-2-yl)-ethyl]-phenylcarbamoyl}-phenyl)-amide | 16 |
| Quinoline-3-carboxylic acid (2-{3-[2-(6,7-dimethoxy-3,4-dihydro-1H-isoquinolin-2-yl)-ethyl]-phenylcarbamoyl}-phenyl)-amide | 17 |
| Quinoline-3-carboxylic acid (2-{4-[2-(7-nitro-3,4-dihydro-1H-isoquinolin-2-yl)-ethyl]-phenylcarbamoyl}-phenyl)-amide | 18 |
| Quinoline-3-carboxylic acid (2-{4-[3-(6,7-dimethoxy-3,4-dihydro-1H-isoquinolin-2-yl)-2-hydroxy-propoxy]-phenylcarbamoyl}-phenyl)-amide | 19 |
| Quinoline-3-carboxylic acid (2-{4-[2-(6,7-dimethoxy-3,4-dihydro-1H-isoquinolin-2-yl)-ethyl]-2-methyl-phenylcarbamoyl}-phenyl)-amide | 20 |
| Quinoline-3-carboxylic acid (2-{4-[2-(6,7-dimethoxy-3,4-dihydro-1H-isoquinolin-2-yl)-ethyl]-2-methoxy-phenylcarbamoyl}-phenyl)-amide | 21 |
| Quinoline-3-carboxylic acid (2-{4-[2-(6,7-dimethoxy-3,4-dihydro-1H-isoquinolin-2-yl)-1-methyl-ethyl]-phenylcarbamoyl}-phenyl)-amide | 22 |
| Quinoline-3-carboxylic acid (2-{3-[3-(6,7-dimethoxy-3,4-dihydro-1H-isoquinolin-2-yl)-propyl]-phenylcarbamoyl}-phenyl)-amide | 23 |
| Quinoline-3-carboxylic acid (2-{4-[2-(7,8-dihydro-5H-[1,3]dioxolo[4,5-g]isoquinolin-6-yl)-ethyl]-phenylcarbamoyl}-phenyl)-amide | 24 |
| Quinoline-3-carboxylic acid (2-{4-[2-(6,7-diethoxy-3,4-dihydro-1H-isoquinolin-2-yl)-ethyl]-phenylcarbamoyl}-phenyl)-amide | 25 |
| Quinoline-3-carboxylic acid (6-{4-[2-(6,7-dimethoxy-3,4-dihydro-1H-isoquinolin-2-yl)-ethyl]-phenylcarbamoyl}-thieno[2,3-b]pyrazin-7-yl)-amide | 26 |
| Isoquinoline-1-carboxylic acid {2-[2-(6,7-dimethoxy-3,4-dihydro-1H-isoquinolin-2-yl)-ethylcarbamoyl]-phenyl}-amide | 27 |
| Quinoline-2-carboxylic acid {2-[2-(6,7-dimethoxy-3,4-dihydro-1H-isoquinolin-2-yl)-ethylcarbamoyl]-phenyl}-amide | 28 |
| Isoquinoline-3-carboxylic acid {2-[2-(6,7-dimethoxy-3,4-dihydro-1H-isoquinolin-2-yl)-ethylcarbamoyl]-phenyl}-amide | 29 |
| Quinoline-3-carboxylic acid {2-[2-(6,7-dimethoxy-3,4-dihydro-1H-isoquinolin-2-yl)-ethylcarbamoyl]-phenyl}-amide | 30 |
| Quinoline-3-carboxylic acid (2-{4-[2-(6,7-dimethoxy-3,4-dihydro-1H-isoquinolin-2-yl)-ethyl]-phenylcarbamoyl}-phenyl)-amide | 31 |
| Quinoline-3-carboxylic acid (2-{4-[2-(6,7-dimethoxy-3,4-dihydro-1H-isoquinolin-2-yl)-ethyl]-phenylcarbamoyl}-5-fluoro-phenyl)-amide | 32 |
| Quinoline-3-carboxylic acid (2-{4-[2-(6,7-dimethoxy-3,4-dihydro-1H-isoquinolin-2-yl)-ethyl]-phenylcarbamoyl}-4-fluoro-phenyl)-amide | 33 |
| Quinoline-3-carboxylic acid (2-{4-[2-(6,7-dimethoxy-3,4-dihydro-1H-isoquinolin-2-yl)-ethyl]-phenylcarbamoyl}-4,5-dimethoxy-phenyl)-amide | 34 |
| Quinoline-3-carboxylic acid (6-{4-[2-(6,7-dimethoxy-3,4-dihydro-1H-isoquinolin-2-yl)-ethyl]-phenylcarbamoyl}-benzo[1,3]dioxol-5-yl)-amide | 35 |

| Chemical Name | Compound No. |
|---|---|
| Quinoline-3-carboxylic acid (2-{4-[2-(6,7-dimethoxy-3,4-dihydro-1H-isoquinolin-2-yl)-ethyl]-phenylcarbamoyl}-5-nitro-phenyl)-amide | 36 |
| Quinoline-3-carboxylic acid (2-{4-[2-(6,7-dimethoxy-3,4-dihydro-1H-isoquinolin-2-yl)-ethyl]-phenylcarbamoyl}-4-methyl-phenyl)-amide | 37 |
| Quinoline-3-carboxylic acid (2-{4-[2-(6,7-dimethoxy-3,4-dihydro-1H-isoquinolin-2-yl)-ethyl]-phenylcarbamoyl}-5-methyl-phenyl)-amide | 38 |
| Quinoline-3-carboxylic acid (2-{4-[2-(6,7-dimethoxy-3,4-dihydro-1H-isoquinolin-2-yl)-ethyl]-phenylcarbamoyl}-4-chloro-phenyl)-amide | 39 |
| Quinoline-3-carboxylic acid (2-{4-[2-(6,7-dimethoxy-3,4-dihydro-1H-isoquinolin-2-yl)-ethyl]-phenylcarbamoyl}-5-chloro-phenyl)-amide | 40 |
| Quinoline-3-carboxylic acid (2-{4-[2-(6,7-dimethoxy-3,4-dihydro-1H-isoquinolin-2-yl)-ethyl]-phenylcarbamoyl}-5-amino-phenyl)-amide | 41 |
| Quinoline-2-carboxylic acid (2-{4-[2-(6,7-dimethoxy-3,4-dihydro-1H-isoquinolin-2-yl)-ethyl]-phenylcarbamoyl}-phenyl)-amide | 42 |
| 5,6,7,8-Tetrahydroquinoline-3-carboxylic acid (2-{4-[2-(6,7-dimethoxy-3,4-dihydro-1H-isoquinolin-2-yl)-ethyl]-phenylcarbamoyl}-phenyl)-amide | 43 |
| Quinoline-3-carboxylic acid (2-{4-[2-(3,4-dihydro-1H-isoquinolin-2-yl)-ethyl]-phenylcarbamoyl}-phenyl)-amide | 44 |
| Quinoline-3-carboxylic acid {2-[4-(6,7-dimethoxy-3,4-dihydro-1H-isoquinolin-2-ylmethyl)-phenylcarbamoyl]-phenyl}-amide | 45 |

The preparation of the compounds of formula (I) is described in WO-A-98/17648.

The pharmaceutically acceptable strong acid used in the process of the present invention is an acid which is capable of forming a salt with the two basic centres in the compounds of formula (I). These are the tetrahydroisoquinoline nitrogen atom and the nitrogen atom in the heterocyclic group $R^{51}$. The pKa values of these two centres can differ significantly and the acid must be strong enough to protonate both. Examples of strong acids suitable for use in the process of the present invention include arylsulphonic acids (such as toluene para-sulphonic acid), alkylsulphonic acids (such as methane sulphonic acid), hydrochloric acid and organic dicarboxylic acids such as malonic acid and succinic acid.

The pharmaceutically acceptable organic solvent used in the process of the invention is typically an alcohol such as ethanol, n-propanol, isopropanol, benzyl alcohol or propylene glycol.

The excess water used in the process of the invention may be introduced into the reaction mixture in step (a) either separately from, or together with, the pharmaceutically acceptable organic solvent. For instance, an aqueous alcohol solution provides both the organic solvent and the water simultaneously. A suitable aqueous alcohol solution contains a 3:1 (v/v) ratio of alcohol to water. A 75% ethanol solution is particularly preferred. The water used in the process of the invention is typically demineralised water. For drug regulatory purposes the water is more preferably purified water.

In the context of the process of the invention the term "excess of water" means sufficient water both to solubilise the acid addition bis-salt of the compound of formula (I) and to achieve the optimum level of hydration of the bis-salt. An excess of water therefore denotes more than a molar excess relative to the number of moles of water of crystallisation in the final hydrate.

The level of hydration is the number of moles of water of crystallisation in the bis-salt and is an integer from 1 to 6. It may be 1, 2, 3, 4, 5 or 6. The hydrate of the invention thus typically possesses a substantially integral number of moles of water of crystallisation. The level of hydration in the solid state depends on factors including the structure of the compound of formula (I) and its capacity, inter alia, for forming attachments to water molecules, for instance via hydrogen bonds.

In step (b) of the process of the invention the mixture is heated until a clear solution forms. This typically entails heating the mixture to a temperature of from 35° C. to the reflux temperature of the organic solvent; for instance to a temperature of from 35° to 70° C., more preferably from 45° C. to 60° C.

In step (c) of the process the solution is filtered while it is warm. This means that the solution is filtered whilst being held at a sufficient temperature to avoid premature precipitation of the desired product. This is typically achieved using warmed glassware, for instance glassware which is maintained at or above the temperature of the solution formed in step (b).

The desired hydrate is recovered in step (d) of the process of the invention by any convenient means. For instance, the filtrate may be diluted with an anti-solvent such as acetone or tetrahydrofuran. For drug regulatory purposes the anti-solvent is preferably pharmaceutically acceptable. A preferred example of a pharmaceutically acceptable anti-solvent is acetone. In one embodiment of the process of the invention step (d) is therefore carried out by adding the warm filtrate produced in step (c) to refluxing acetone, preferably refluxing pre-filtered acetone.

The process of the present invention is preferably carried out in an atmosphere having a relative humidity of from 40% to 80%, more preferably from 50% to 80%.

The hydrate produced by the process of the present invention has been shown in hygroscopicity studies to lose water on heating in vacuo, but it can be restored to its original level of hydration in a moist atmosphere. The hydrate has greater storage stability (e.g. shelf life) and better dissolution characteristics (i.e. a higher rate of dissolution) in pharmaceutical formulation media than the conventional indeterminate hydrates obtained by previous processes.

The hydrate of the present invention is preferably the hexahydrate of the bismesylate of quinoline-3-carboxylic acid (2-{4-[2-(6,7-dimethoxy-3,4-dihydro-1H

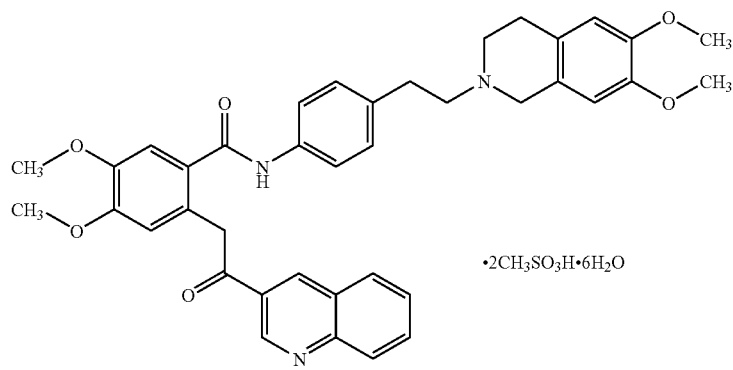

-isoquinolin-2-yl)-ethyl]-phenylcarbamoyl}-4,5-dimethoxyphenyl)-amide. This compound, which is compound 34 in the above table, has the following structure:

The above hexahydrate is preferably prepared by a process which comprises:

(a') combining, with warming, quinoline-3-carboxylic acid (2-{4-[2-(6,7-dimethoxy-3,4-dihydro- 1H-isoquinolin-2-yl)-ethyl]-phenylcarbamoyl}-4,5-dimethoxy-phenyl)-amide, ethanol and excess water, and adding methanesulphonic acid to the mixture;

(b') warming the mixture until a clear solution forms;

(c') filtering the solution while it is warm, to form a filtrate; and (d') recovering the desired hexahydrate from the filtrate.

In step (a') an aqueous ethanol solution may be used. Alternatively, absolute ethanol and water may be introduced separately into the reaction system. The volume ratio of ethanol to water in either case is preferably about 3:1. The water is typically demineralised water.

In step (b') the mixture is typically warmed to a temperature of from 35° C. to reflux, preferably about 55° C.

In step (c') the solution is preferably filtered through warm glassware and washed through with a mixture of ethanol and water, typically into a dropping funnel maintained at about the temperature of the filtrate.

Step (d') is typically carried out by adding the filtrate to a stirred refluxing anti-solvent, preferably filtered acetone. The resultant suspension is then refluxed for several hours, cooled and the hexahydrate is then collected as a solid.

Another specific example of a hydrate of the present invention is the monohydrate of the bismesylate of compound 31, namely the monohydrate of the bismesylate of quinoline-3-carboxylic acid (2-{4-{2-(6,7-dimethoxy-3,4-dihydro-1H-isoquinolin-2-yl) -ethyl}-phenylcarbamoyl}-phenyl)amide.

The hydrates of the present invention provide a convenient means for formulating the bis-salts of the compounds of formula (I) into pharmaceutical compositions. Preferred composition are liquid compositions for oral or parenteral delivery. The hydrates may thus be used in all the pharmaceutical applications envisaged for the compounds of formula (I) and their salts as described in WO-A-98/07648. These applications are discussed below.

Cancer cells which exhibit multi-drug resistance, referred to as MDR cells, display a reduction in intracellular drug accumulation compared with the corresponding drug-sensitive cells. Studies using in vitro derived MDR cell lines have shown that MDR is often associated with increased expression of a plasma membrane glycoprotein (P-gp) which has drug binding properties. P-gp is thought to function as an efflux pump for many hydrophobic compounds, and transfection studies using cloned P-gp have shown that its overexpression can confer the MDR phenotype on cells: see, for example, Ann. Rev. Biochem 58 137-171 (1989).

A major function of P-gp in normal tissues is to export intracellular toxins from the cell. There is evidence to suggest that overexpression of P-gp may play a clinical role in multidrug resistance. Increased levels of P-gp mRNA or protein have been detected in many forms of human cancers—leukaemias, lymphomas, sarcomas and carcinomas. Indeed, in some cases P-gp levels have been found to be increased in tumour biopsies obtained after relapse from chemotherapy.

Inhibition of P-gp function in P-gp mediated MDR has been shown to lead to a net accumulation of anti-cancer agent in the cells. For example, Verapamil a known calcium channel blocker was shown to sensitise MDR cells to Vinca alkaloids in vitro and in vivo: *Cancer Res.,* 41, 1967-1972 (1981). The proposed mechanism of action involves competition with the anti-cancer agent for binding to the P-gp. A range of structurally unrelated resistance-modifying agents acting by this mechanism have been described such as tamoxifen (Nolvadex:ICI) and related compounds, and cyclosporin A and derivatives.

Compounds of formula I as defined above and their pharmaceutically acceptable salts have been found in biological tests to have activity as inhibitors of P-gp. They can be used to modulate MDR, in particular P-gp mediated MDR. The results are set out in Example 1 which follows. As P-gp inhibitors the compounds may be used as multi-drug resistance modifying agents, also termed resistance-modifying agents, or RMAs. The compounds can modulate, e.g. reduce, or eliminate multi-drug resistance, especially that which is P-gp mediated.

The compounds can be used in a method of potentiating the cytotoxicity of an agent which is cytotoxic to a tumour cell. Such a method comprises, for instance, administering one of the compounds to the tumour cell whilst the tumour cell is exposed to the cytotoxic agent in question. The therapeutic effect of a chemotherapeutic, or antineoplastic, agent may thus be enhanced. The multi-drug resistance of a tumour cell to a cytotoxic agent during chemotherapy may be reduced or eliminated.

The compounds can also be used in a method of treating a disease in which the responsible pathogen exhibits multi-drug resistance, especially P-gp mediated multi-drug resistance for instance multi-drug resistant forms of malaria (*Plasmodium falciparum*), tuberculosis, leishmaniasis and amoebic dysentery. Such a method comprises, for instance, administering one of the compounds with (separately, simultaneously or sequentially) the drug to which the pathogen concerned exhibits multi-drug resistance. The therapeutic effect of a drug directed against a multidrug resistant pathogen may thus be potentiated.

A human or animal patient harbouring a tumour may be treated for resistance to a chemotherapeutic agent by a method comprising the administration thereto of one of the compounds of formula (I) as defined above. The compound is administered in an amount effective to potentiate the cytotoxicity of the said chemotherapeutic agent. Examples of chemotherapeutic or antineoplastic agents which are preferred in the context of the present invention include Vinca alkaloids such as vincristine and vinblastine; anthracycline antibiotics such as daunorubicin and doxorubicin; mitoxantrone; actinomycin D; taxanes e.g. taxol; epipodophyllotoxins e.g. etoposide and plicamycin.

The compounds of formula (I) as defined above may also be used in a method of enhancing the absorption, distribution, metabolism and/or elimination characteristics of a therapeutic agent, which method comprises administering to a patient, separately, simultaneously or sequentially, one of the compounds and the said therapeutic agent. In particular this method may be used to enhance the penetration of the therapeutic agent into the central nervous system, or to enhance the oral absorption of the therapeutic agent.

For instance, the compounds can be used in a method of facilitating the delivery of drugs across the blood brain barrier, and in the treatment of AIDS or AIDS related complex. A human or animal patient in need of such treatment may be treated by a method comprising the administration thereto of one of the present compounds.

The hydrates of the present invention can be formulated for administration in a variety of dosage forms, for example orally such as in the form of liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration is such as to achieve the delivery of from 0.001 to 50 mg/kg body weight, most commonly in the range of 0.01 to 5 mg/kg, of the compound of formula (I). Such a dosage may be given, for example, from 1 to 5 times daily by bolus infusion, infusion over several hours and/or repeated administration.

The hydrates of the present invention are formulated for use as a pharmaceutical or veterinary composition also comprising a pharmaceutically or veterinarily acceptable carrier or diluent. The compositions are typically prepared following conventional methods and are administered in-a pharmaceutically or veterinarily suitable form. An agent for use as a modulator of multi-drug resistance comprising a hydrate of the present invention is therefore provided.

The present hydrates may be administered in any conventional form, for instance as follows:

A) Orally, for example, as aqueous or oily suspensions, liquid solutions, emulsions, syrups or elixirs. Compositions intended for oral use may be prepared according to any method known in the art for the manufacture of pharmaceutical compositions and such compositions may contain one or more agents selected from sweetening agents, flavouring agents, colouring agents and preserving agents in order to provide pharmaceutically elegant and palatable preparations.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occuring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents.

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

Daily dosages can vary within wide limits and will be adjusted to the individual requirements in each particular case. In general, for administration to adults, an appropriate daily dosage is in the range of about 5 mg to about 500 mg of the compound of formula (I), although he upper limit may be exceeded if expedient. The daily dosage can be administered as a single dosage or in divided dosages.

The invention will be further described in the Examples which follow:

EXAMPLE 1

Preparation of the bismesylate hexahydrate of Compound 34

Quinoline-3-carboxylic acid (2-{4-[2-(6,7-dimethoxy-3,4-dihydro-1H-isoquinolin-2-yl)-ethyl]-phenylcarbamoyl}-4,5-dimethoxy-phenyl)-amide (10.33 g, 16 mmol) was stirred in a mixture of ethanol (62 ml, 6 volumes) and demineralised water (20.6 ml, 2 volumes) and methanesulphonic acid (3.38 g, 35.2 mmol) was added. The mixture was heated to 55° C. to give a clear orange coloured solution and filtered under vacuum through a preheated funnel into a dropping funnel maintained at a about 55° C. This was followed by a 1:1 wash of ethanol and demineralised water (2×20 ml, 4 volumes) at about 55° C.

The combined filtrate and washes were added over about 20 minutes to stirred, refluxing acetone (310 ml, 30 volumes) to give a sticky yellow solid. After refluxing the mixture for a further 1 hour, the yellow suspension was cooled for 2 hours in an ice-bath to about −5° C. The product was collected by filtration, washed with filtered acetone (3×50 ml) and pulled dry for about 30 minutes. The pale yellow solid was transferred to an open dish and allowed to dry overnight in a gentle current of air at ambient temperature and humidity to give the title compound.

Weight: 13.86 g; yield: 91.5% theory for hexahydrate.

The water content by Karl Fischer was 12.54% (theory for hexahydrate: 11.41%).

The ratio of methanesulphonic acid to base by $^1$H NMR was 1.93: 1 (theory requires 2:1).

The purity by HPLC was 99.7% a/a.

Elemental analyses were consistent with $C_{38}H_{38}N_4O_6 \cdot 2CH_3SO_3H$, 12.54% water.

Found: C=50.35%; H=6.15%; N=5.85%; S=6.71%. [$C_{40}H_{46}N_4O_{12}S_2$, 12.54% $H_2O$ requires C=50.09%; H=6.24%; N=5.84%; S=6.68%.]

EXAMPLE 2

Preparation of the bismesylate monohydrate of Compound 31

A suspension of quinoline-3-carboxylic acid (2-{4-{2-(6,7-dimethoxy-3,4-dihydro-1H-isoquinolin-2-yl)-ethyl]-phenylcarbamoyl}-phenyl)-amide (3.0 g, 5.11 mmol) in a mixture of ethanol (18 ml, 6 volumes) and water (6 ml, 2 volumes) was warmed to about 50° C. and methane sulphonic acid (1.08 g, 11.2 mmol) was added to give a pale orange coloured solution. This was filtered and added rapidly to stirred, refluxing acetone (60 ml, 20 volumes). The flask and filter were washed with a 1:1 mixture of ethanol and demineralised water (6 ml, 2 volumes) at about 50° C. and this was added to the refluxing acetone. After refluxing the mixture for 2 hours, the suspension was cooled to ambient temperature and the pale yellow product was collected by filtration, washed with acetone (9 ml) and dried in vacuum at ambient temperature.

The yield was 3.8 g (93.3% for monohydrate).

The water content, by Karl Fischer, was 2.42% (theory for monohydrate: 2.26%).

The purity by HPLC was 100% a/a.

EXAMPLE 3

Hygroscopicity and Dehydration/Re-Hydration Study

The hexahydrate produced in Example 1 was analysed as follows. Four desiccator cabinets were prepared to contain open dishes of the following saturated salt solutions, to achieve the following approximate relative humidities (RH).

| % RH at Ambient Temp. | Saturated Salt Solution |
| --- | --- |
| 33% | $MgCl_2 \cdot 6H_2O$ |
| 60% | NaBr |
| 75% | NaCl |
| 95% | $KNO_3$ |

Dehydration of samples was carried out by storing them over silica gel or over $P_2O_5$ at reduced pressure (65 mm Hg). All studies were performed at ambient laboratory temperature (15-22° C.).

Hygroscopicity Study

Pre-equilibrated weighing bottles and lids (stored at 33% RH for a minimum of 24 hours) were weighed on a tared 5-figure analytical balance, and the weight recorded. To these the hydrate was added (approx 2 g), the weight recorded and the difference (the accurate weight of the drug substance) calculated. The weighing bottles, lids and contents were then transferred to the 33% RH cabinet, with the lids removed and placed to the side.

At appropriate times, the lids were replaced and the weight measured. After weighing, the samples were gently agitated and placed back in the 33% RH cabinet, again with the lid removed and placed to one side. This process continued until all % weight changes for all samples were seen to have reached stable end-points. When stable end-points. When stable end-points were observed, the samples were stepped up to the next % RH cabinet by transferring the drug to pre-equilibrated weighing bottles, recording their weight as before. Samples were stored progressively at 33% RH, 60% RH, 75% RH and 95% RH.

Dehydration/Re-Hydration Study

During this study, samples were dispensed to pre-equilibrated weighing bottles as in the hygroscopicity study, and were then stored over silica gel without reduced pressure, then over silica gel under reduced pressure (65 mm Hg) to dehydrate the hydrate. Once a stable weight was achieved over $P_2O_5$, samples were re-hydrated by storing them at 33% RH to 95% RH, in parallel with the hygroscopicity study as described above.

Determination of Water Content

Water contents were measured by coulometric KF (Karl Fischer) titration.

IR Analysis

Samples of the hydrate were submitted for IR analysis (ATR) at the end of the dehydration study and at the ends of the re-hydration and hygroscopicity studies.

Results

Weight Change

Results for the hygroscopicity study and the dehydration/re-hydration study are shown in Table 1.

TABLE 1

Dehydration/Rehydration and Hygroscopicity
Results up to 60% RH
(Results in brackets are KF moisture results, % w/w)

|  |  | Cumulative % change | |
|---|---|---|---|
| Condition | Cumulative time (h) | Dehydration/ Rehydration | Hygroscopicity* |
| silica, no vacuum. | 3.00 | (12.53) −2.29 |  |
|  | 8.50 | −3.58 |  |
|  | 24.50 | −5.92 |  |
|  | 30.50 | −6.39 |  |
|  | 56.00 | −8.06 |  |
|  | 80.00 | −8.50 |  |
|  | 237.50 | −8.96 |  |
|  | 288.50 | −9.07 |  |
| silica, with vacuum. | 308.00 | −9.07 |  |
|  | 401.00 | −8.76 |  |
| $P_2O_5$ with vacuum | 425.00 | −10.85 |  |
|  | 452.00 | −11.00 |  |
|  | 476.75 | −11.19 |  |
|  | 570.25 | −11.43 |  |
|  | 641.00 | −11.35 |  |
|  | 760.50 | −11.51 |  |
|  | 904.25 | −11.46 |  |
|  | 1071.00 | −11.54 |  |
|  | 1144.00 | −11.48 |  |
| 33% RH | 1147.25 | (3.82) −6.61 | (12.45) −0.17* |
|  | 1150.75 | −4.80 | −0.22 |
|  | 1168.00 | −2.47 | −0.47 |
|  | 1240.75 | −0.68 | −0.37 |
|  | 1268.50 | −0.62 | −0.42 |
|  | 1312.50 | −0.62 | −0.49 |
|  | 1431.25 | −0.83 | −0.63 |
|  | 1502.25 | −0.66 | −0.51 |
|  | 1672.50 | −0.91 | −0.70 |
|  | 1741.50 | −0.97 | −0.76 |
| 60% RH | 1744.50 | 0.19 | 0.12 |
|  | 1746.50 | 0.31 | 0.13 |
|  | 1762.50 | 0.30 | 0.08 |
|  | 1835.75 | 0.54 | 0.27 |

TABLE 1-continued

Dehydration/Rehydration and Hygroscopicity
Results up to 60% RH
(Results in brackets are KF moisture results, % w/w)

|  |  | Cumulative % change | |
|---|---|---|---|
| Condition | Cumulative time (h) | Dehydration/ Rehydration | Hygroscopicity* |
|  | 1932.25 | 0.64 | 0.37 |
|  | 2101.50 | 0.86 | 0.56 |
|  | 2147.75 | 0.62 | 0.34 |
|  | 2273.75 | 0.61 | 0.34 |
|  | 2410.25 | 0.51 | 0.27 |
| 75% RH | 2417.25 | 1.18 | 0.87 |
|  | 2434.25 | 1.21 | 0.88 |
|  | 2441.25 | 1.26 | 0.88 |
|  | 2482.00 | 1.23 | 0.92 |
|  | 2577.75 | 1.35 | 1.00 |
|  | 2609.75 | 1.38 | 0.96 |
|  | 2681.25 | 1.41 | 1.08 |
|  | 2770.25 | 1.36 | 1.01 |
|  | 2817.75 | 1.44 | 1.09 |
| 95% RH | 2825.25 | 2.28 | 1.85 |
|  | 2841.75 | 2.73 | 2.23 |
|  | 2915.75 | 3.06 | 2.57 |
|  | 2937.75 | 3.21 | 2.71 |
|  | 2991.25 | 3.25 | 2.82 |
|  | 3082.25 | 3.86 | 3.28 |
|  | 3130.00 | 4.12 | 3.51 |
|  | 3182.25 | 3.99 | 3.39 |
|  | 3252.25 | 4.19 | 3.62 |
|  | 3350.25 | 4.22 | 3.65 |
|  | 3422.25 | 4.35 | 3.64 |
|  | 3636.25 | 5.31 | 4.12 |
|  | 4332.75 | (15.81) 5.58 | (15.35) 4.45 |

*The actual cumulative storage time for the hygroscopicity sample is the tabulated value minus 1144 hours.

IR Results

IR spectra for the samples taken at the end of the re-hydration and hygroscopicity studies showed no significant differences in the wavenumber and relative intensities of the main bands.

The IR spectrum of the sample taken at the end of the dehydration study showed the expected loss of the major, broad water band at about 3500 cm$^{-1}$. Other than this the spectrum was similar to those recorded after the re-hydration and hygroscopicity studies with some small differences in relative intensities and resolution. The main differences in relative intensity occured at about 1650, 1200 and 850 cm$^{-1}$.

Conclusion

Dehydration of the hydrate of Example 1 over increasing desiccating conditions results in a relatively rapid loss of water. The final weight change (−11.5%) is similar to the initial water content of the sample (12.5%). Re-hydration at 33% RH results in a rapid restoration of the weight lost. Storing the re-hydrated and untreated materials at progressively higher RH values results in only small increases in sample weight. Both samples show less than 2% (absolute) weight increases between storage at 33% RH and at the end of storage at 75% RH.

The hydrate of Example 1 thus displays dehydration/re-hydration properties consistent with its existing as a stable hydrate. This is characterised by its rapidly regaining approximately the same amount of water on re-hydration that it lost on dehydration. On storage at progressively higher RH values it displays no evidence of hygroscopicity, again consistent with its existing as a stable hydrate.

From the data generated the behaviour of the material is in line with its existing as a hexahydrate. The theoretical water content for the hydrate of Example 1 is 11.4% w/w. Thus a water content of about 12.5% w/w, the initial value before dehydration, could correspond to a damp hexahydrate. (A water content of 12.5% w/w would correspond to 6.7 moles of water per mole of bismesylate.)

When the material is dehydrated and then re-hydrated at 33% RH the net weight change is about −1%, corresponding to a notional water content of about 11.5%. This is consistent with the dehydrated material recovering its 6 moles of water but not the extra, non-specific, loosely-bound moisture. Upon re-hydration the material displays virtually identical properties to the material which had not been dehydrated in terms of weight change and final IR spectra, indicating that dehydration probably results in an "open", dehydrated crystal structure which does not undergo collapse or re-arrangement.

The results thus indicate that the hydrate of Example 1 is a stable hexahydrate with a small amount of additional, loosely bound water. In this hydrated form, the material does not display the hygroscopic properties exhibited by the bismesylate of compound 34 produced by conventional techniques, for instance as described in WO98/07648.

EXAMPLE 4

Testing of Compounds of Formula (I) and Their Salts as Modulators of MDR

Materials and Methods

The EMT6 mouse mammary carcinoma cell line and the MDR resistant subline AR 1.0 were cultured in RPMI 1640 medium containing 10% foetal calf serum and 2 mM glutamine at 37° C. in 5% $CO_2$. Cells were passaged between 1 in 200 and 1 in 2000 in the case of the parental cell line and between 1 in 20 and 1 in 200 in the case of the MDR resistant subline, after trypsinisation (0.25% trypsin, 0.2 $gl^{-1}$, EDTA).

1. Drug Accumulation Assay

AR 1.0 cells were seeded 48 hours prior to assay into 96 well opaque culture plates (Canberra Packard). The assay medium contained a mixture of tritiated Daunorubicin (DNR) (0.3 mCi/Ml), a cytotoxic agent, and unlabelled DNR ((2 mM). Compounds of formula I were serially diluted in assay medium over a range of concentrations from 0.508 nM to 10 mM. The cells were incubated at 37° C. for 1 hr before washing and determination of cell associated radioactivity. Results are expressed as an $IC_{50}$ for accumulation where 100% accumulation is that observed in the presence of the known RMA verapamil at a concentration of 100 mM.

The results are set out in the following Table A.

TABLE A

| Compound No. | $IC_{50}$(mM) Accumulation |
|---|---|
| 1 | 0.425 |
| 2 | >10 |
| 3 | 0.087 |
| 4 | 0.37 |
| 5 | >10 |
| 6 | 0.431 |
| 7 | 0.098 |
| 8 | 0.213 |
| 9 | 0.113 |
| 10 | 0.203 |
| 11 | 0.453 |
| 12 | 0.207 |
| 13 | 1.89 |
| 14 | 0.347 |

TABLE A-continued

| Compound No. | $IC_{50}$(mM) Accumulation |
|---|---|
| 15 | 2.27 |
| 16 | >10 |
| 17 | 0.593 |
| 18 | 6.955 |
| 19 | 0.038 |
| 20 | 0.061 |
| 21 | 0.071 |
| 22 | 0.135 |
| 23 | 6.424 |
| 24 | 1.679 |
| 25 | 0.389 |
| 26 | 8.672 |
| 27 | 2.0 |
| 28 | 1.2 |
| 29 | 1.8 |
| 30 | 10 |
| 31 | 0.05 |
| 32 | 0.022 |
| 33 | 0.019 |
| 34 | 0.064 |
| 35 | 0.084 |
| 36 | 0.015 |
| 37 | 0.36 |
| 38 | 0.094 |
| 39 | 0.014 |
| 40 | 0.18 |
| 41 | 1.0 |
| 42 | 0.8 |
| 43 | 0.097 |
| 44 | 0.32 |
| 45 | 0.04 |

2. Potentiation of Doxorubicin Toxicity (a) Selected compounds of formula (I) were examined for their ability to potentiate the toxicity of doxorubicin in AR 1.0 cells. In initial proliferation assays compounds were titrated against a fixed concentration of doxorubicin (0.34 mm) which alone is non-toxic to AR 1.0 cells. After a four day incubation with doxorubicin proliferation was measured using the colorimetric sulphorhodamine B assay (Skehan et al; J Natl. Cancer Inst. 82 pp 1107-1112 (1990)). The results are shown in Table B.

(b) Cells were cultured for four days with a titration of doxorubicin (0.263 nM-17.24 mM) in the presence of a fixed concentration of each compound. Proliferation was quantified as described by Skehen et al, loc cit. The $IC_{50}$ (concentration required to reduce proliferation to 50% of the untreated controls) for doxorubicin alone and with each compound were derived and used to calculate the potentiation index (PI):

$$PI = \frac{IC_{50} \text{ for Doxorubicin alone}}{IC_{50} \text{ for Doxorubicin plus } RMA}$$

The results are shown in Tables C1 and C2.

TABLE B

| Compound No. | Compound Toxicity ($IC_{50}$ mM) | Toxicity with Cytotoxic Agent ($IC_{50}$ mM) |
|---|---|---|
| 27 | 40 | 1.0 |
| 28 | 40 | 0.55 |
| 29 | 30 | 0.3 |
| 33 | 0.32 | 0.005 |

TABLE B-continued

| Compound No. | Compound Toxicity (IC$_{50}$ mM) | Toxicity with Cytotoxic Agent (IC$_{50}$ mM) |
|---|---|---|
| 34 | 0.93 | 0.0018 |
| 35 | 0.9 | 0.0014 |
| 36 | 0.31 | 0.0038 |
| 37 | 8.6 | 0.015 |
| 38 | 6.7 | 0.005 |
| 39 | 7.0 | 0.005 |
| 40 | 7.4 | 0.04 |
| 41 | 36.8 | 4.4 |
| 42 | 1.7 | 0.07 |
| 43 | 9.5 | 0.05 |
| 44 | 7.7 | 0.00035 |
| 45 | 9.2 | 0.022 |

TABLE C1

| Compound No. | Potentiation Index at RMA Concentration | | | | |
|---|---|---|---|---|---|
| | 100 nM | 50 nM | 30 nM | 20 nM | 10 nM |
| 3 | 601 | 307 | 159 | | 11 |
| 4 | 45 | 2.99 | 1.93 | | 1.45 |
| 6 | 68 | 19 | 7.4 | 3.4 | 1.4 |
|  | 171 | 149 | 95 | | 11 |
| 7 | 168 | 97 | 35 | | 3 |
| 8 | 175 | 85 | 23 | | 2 |
| 9 | 185 | 143 | 142 | | 13 |
| 10 | 81 | 15 | 4 | | 1.5 |
| 11 | 25 | 4.4 | 1.6 | 1.3 | 1.0 |
| 12 | 79 | 46 | 15 | 8 | 1.8 |
| 14 | 60 | 7 | 4 | | 1 |
| 17 | 13.7 | 3.4 | 1.3 | | 1.0 |
| 19 | | | 34 | | 16 |
| 20 | 33 | 14 | 3 | | 3 |
| 21 | 2.2 | 1.1 | | | |
| 23 | 1.4 | 1.2 | 1.1 | | |
| 24 | 116 | 37 | 1.9 | | 1 |
| 25 | 50 | 28 | 7 | | 1.4 |

TABLE C2

| Compound No. | Potentiation Index at RMA Concentration: | | | | |
|---|---|---|---|---|---|
| | 500 nM | 300 nM | 100 nM | 30 nM | 10 nM |
| 31 | | 150 | 120 | 67 | 15 |
| 32 | | | 100 | 100 | 38 |
| 33 | | | 94 | 60 | 16 |
| 34 | | 280 | 225 | 78 | |
| 35 | | | | 188 | 43 |
| 36 | | | | 300 | 90 |
| 37 | | | | 36 | 2.1 |
| 38 | | | | 68 | 6 |
| 39 | | | | 57 | 6 |
| 40 | | | | 6 | 5 |
| 41 | | | | 1 | 1 |
| 44 | | | 112 | 18 | 2.2 |
| 45 | | | | 7.2 | 1.3 |

3. Potentiation of Toxicity of Various Cytotoxic Agents

The potentiation indices of a selection of compounds using a variety of cell lines and a variety of cytotoxics other than doxorubicin were measured following the protocol described above for doxorubicin, and the results are shown in Table D.

TABLE D

| Compound No. | Cell line | Cytotoxic | Potentiaton Index at RMA Concentration | | |
|---|---|---|---|---|---|
| | | | 50 nM | 30 nM | 10 nM |
| 3 | 2780AD | Taxol | 1126 | 425 | 18 |
| 3 | H69/LX4 | Vincristine | 356 | 79 | 2 |
| 3 | AR 1.0 | Taxol | 407 | 308 | 50 |
| 6 | H69/LX4 | Taxol | 9 | 3 | 1 |
| 7 | H69/LX4 | Taxol | 877 | 236 | 2.2 |
| 34 | AR 1.0 | Etoposide | 51 | 45 | 26 |

The invention claimed is:

1. A process for producing a hydrate of an acid addition salt of a compound of formula (I):

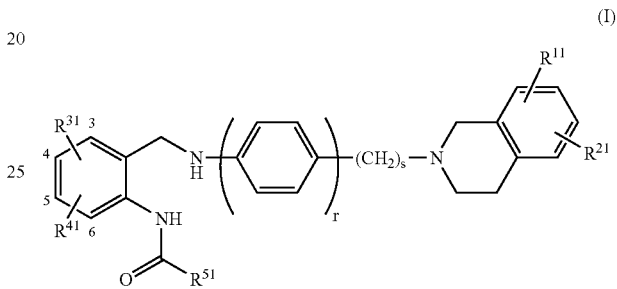

wherein $R^{11}$ and $R^{21}$, which may be the same or different, are each hydrogen or alkoxy;

$R^{31}$ and $R^{41}$, which may be the same or different, are each independently selected from H, $C_1$-$C_6$ alkyl, $CF_3$, a halogen, $NH_2$, $NO_2$, NHOH, $C_1$-$C_6$ alkoxy, hydroxy and phenyl; or $R^{31}$ and $R^{41}$, when situated on adjacent carbon atoms, form together with the carbon atoms to which they are attached a benzene ring or a methylenedioxy substituent;

$R^{51}$ is a group selected from pyridine, quinoline, isoquinoline, 5,6,7,8-tetrahydroquinoline and 5,6,7,8-tetrahydroisoquinoline, the group being unsubstituted or substituted by $C_1$-$C_6$ alkyl or $C_1$-$C_6$ alkoxy;

r is 0 or 1, and s is 1, 2, or 3;

which process comprises:

(a) combining, in any order, a compound of formula (I) as defined above, a pharmaceutically acceptable organic solvent, an excess of water and a pharmaceutically acceptable strong acid to form a mixture;

(b) warming the mixture until a clear solution forms;

(c) filtering the solution while it is warm, to yield a filtrate; and (d) recovering the hydrate as defined above from the filtrate.

2. A process according to claim 1 wherein the hydrate is recovered by diluting the filtrate with an anti-solvent.

3. A process according to claim 2 wherein the anti-solvent is pre-filtered acetone.

4. A process according to claim 1 wherein the pharmaceutically acceptable solvent is an alcohol.

5. A process according to claim 4 wherein the alcohol is selected from ethanol, npropanol, isopropanol, benzyl alcohol and propylene glycol.

6. A process according to claim 1 wherein the pharmaceutically acceptable strong acid is methanesulphonic acid.

7. A process according to claim 1 wherein the compound of formula (I) is quinoline-3-carboxylic acid (2-{4-[2-(6,7-dimethoxy-3,4-dihydro-1H-isoquinolin-2-yl)-ethyl]-phenylcarbamoyl}-4,5-dimethoxyphenyl) amide.

8. A hydrate of an acid addition salt of a compound of formula I as defined in claim 1, formed with a pharmaceutically acceptable strong acid, wherein the hydrate incorporates x moles of a water of crystallisation per mole of the compound, in which x is an integer from 1 to 6.

9. A hydrate according to claim 8 wherein the pharmaceutically acceptable strong acid is methanesulphonic acid.

10. A hydrate according to claim 8 which is the hexahydrate of the bismesylate of quinoline-3-carboxylic acid (2-{4-[2-(6,7-dimethoxy-3,4-dihydro-1H-isoquinolin-2-yl)-ethyl]-phenylcarbamoyl}-4,5-dimethoxyphenyl) amide.

11. A hydrate which is obtainable by a process as defined in claim 1.

12. A pharmaceutical or veterinary composition comprising a hydrate as defined in claim 8 and a pharmaceutically or veterinarily acceptable carrier or diluent.

13. A hydrate as defined in claim 8 for use in a method of medical treatment of the human or animal body by therapy.

* * * * *